US006762201B1

(12) United States Patent
Miller et al.

(10) Patent No.: US 6,762,201 B1
(45) Date of Patent: Jul. 13, 2004

(54) FAB I INHIBITORS

(75) Inventors: William H. Miller, Collegeville, PA (US); Kenneth A. Newlander, West Chester, PA (US); Mark A. Seefeld, Collegeville, PA (US)

(73) Assignee: Affinium Pharmaceuticals, Inc., Toronto (CA)

( * ) Notice: Subject to any disclaimer, the term of this patent is extended or adjusted under 35 U.S.C. 154(b) by 194 days.

(21) Appl. No.: 10/089,739

(22) PCT Filed: Oct. 6, 2000

(86) PCT No.: PCT/US00/27591

§ 371 (c)(1),
(2), (4) Date: Apr. 3, 2002

(87) PCT Pub. No.: WO01/26654

PCT Pub. Date: Apr. 19, 2001

Related U.S. Application Data

(60) Provisional application No. 60/158,529, filed on Oct. 8, 1999.

(51) Int. Cl.$^7$ .................. A61K 31/4045; C07D 209/14
(52) U.S. Cl. ....................................... 514/419; 548/496
(58) Field of Search ........................... 548/496; 514/419

(56) References Cited

U.S. PATENT DOCUMENTS

| | | |
|---|---|---|
| 3,828,068 A | 8/1974 | Minieri |
| 4,154,943 A | 5/1979 | Kuehne |
| 4,977,159 A | 12/1990 | Sevrin et al. |
| 5,614,551 A | 3/1997 | Dick et al. |
| 5,624,941 A | 4/1997 | Barth et al. |
| 5,932,743 A | 8/1999 | Collini et al. ............ 548/508 |
| 5,985,867 A | 11/1999 | Rodgers et al. |
| 6,346,391 B1 | 2/2002 | Oethinger et al. |
| 6,372,752 B1 | 4/2002 | Staveski et al. |
| 6,451,816 B1 | 9/2002 | Biedermann et al. |
| 6,469,046 B1 | 10/2002 | Daines et al. |
| 6,503,903 B1 | 1/2003 | Miller et al. |
| 6,503,908 B1 | 1/2003 | Maw |
| 6,559,172 B1 | 5/2003 | Heerding et al. |
| 6,573,272 B1 | 6/2003 | Miller et al. |

FOREIGN PATENT DOCUMENTS

| | | |
|---|---|---|
| WO | WO 95/18619 | 7/1995 |
| WO | WO 96/00730 | 1/1996 |
| WO | WO 97/48696 | 12/1997 |
| WO | WO 9857952 A | 12/1998 |
| WO | WO 01/26652 | 4/2001 |
| WO | WO 01/26654 A1 | 4/2001 |
| WO | WO 01/27103 A1 | 4/2001 |
| WO | WO 01/48248 | 7/2001 |
| WO | WO 02/42273 | 5/2002 |
| WO | WO 02/48097 | 6/2002 |

OTHER PUBLICATIONS

Supplementary European Search Report. EP 00 97 3420, Sep. 23, 2002.
Jianxiong, L. et al,: "Synthesis and Antistaphylococcal Activity of Nematophin and Its Analogs" Bioorganic & Medicinal Chemistry Letters, Oxford, GB, vol. 7, No. 10, May 20, 1997, pp. 1349–1352, XP004136332 ISSN:0960–894X.
Abou–Gharbia et al., "Psychotropic Agents: Synthesis and Antipysychotic Activity of Substituted B–Carbolines," J. Med. Chem., 30(6):1100–1105 (1987).
Ahsan et al., "Reserpine Anlogues: Synthesis of B–Carboline Derivatives," J. Chem. Soc., pp. 3928–3930 (1963).
Database CA on STN, AN 7:66733, Rosenmund et al., "Chemistry of indole II . . . ," Chem. Ber. 103(2): 496–509 (1970).
Database CAOLD on STN, AN CA51:10524d, Hellman et al., "N–Mannich bases (VI) condensation . . . ," Direct Submission (1953).
Database CAPLUS on STN, An 1977:439214. Misztal et al., "Synthesis and pharmacologic properties of pyridoyl . . . ," Arch Immuno Ther Exp. 24(6): 851–862 (1976).
DATABASE Crossfire Beilstein, 1966, Database accession No. 2819049, 2819050, XP 002216033.
Himmer et al., "Synthesis and Antibacterial in Vitro Activity of Novel Analogues of Nematophin," Bioorganic & Medicinal Chemistry Letters, 8(15): 2045–2050 (Aug. 1998).
Miller et al., Discovery of Aminopyridine–Based Inhibitors of Bacteriol Enoyl–ACP Reductase (FABI); J. Med. Chem. 2002, vol. 45, pps. 3246–3256.
Misztal et al., "Synthesis and Pharmacologic Properties of Pyridol Derivatives of 3–Methylaminoindole 2–Methyltryptamine and Isotryptamine," Archivum Immnologiae et Therapiae Experimentalis, 24(6): 851–852 (1976).
Pachter et al., "The Chemistry of Hortiamine and 6–Methoxyhetsinine," J. Amer. Chem., 83:635–642 (1961).
Rehse et al., "Dopaminanaloge 1,2,3,4–Tetrahydro–B–Carboline," Arch. Pharm., 311(1):11–18 (1978).
Shoji et al., "Two Novel Alkaloids from Evodia Rutaecarpa," J. Natural Products, 52(5):1160–1162 (1989).
U.S. patent application Ser. No. 10/407,028, filed Apr. 4, 2003, Methods of Agonizing and Antagonizing Fab K, pending.
U.S. patent application Ser. No. 09/959,172, filed Apr. 19, 2000, Fab I Inhibitors.
U.S. patent application Ser. No. 10/292,687, filed Nov. 12, 2002, Fab I Inhibitors, pending.
U.S. patent application Ser. No. 09/979,560, filed May 24, 2000, Disubstituted Imidazoles Useful in the Treatment of Bacterial Infections.
U.S. patent application Ser. No. 10/339,092, filed Jan. 9, 2003, Disubstituted Imidazoles Useful in the Treatment of Bacterial Compounds, pending.
U.S. patent application Ser. No. 09/980,369, filed Jun. 1, 2000, Antibacterial Compounds.
U.S. patent application Ser. No. 10/429,923, filed May 5, 2003, Antibacterial Compounds, pending.
U.S. patent application Ser. No. 10/089,755, filed Oct. 6, 2000, Fab I Inhibitors, pending.
U.S. patent application Ser. No. 10/089,740, filed Oct. 6, 2000, Fab I Inhibitors.

*Primary Examiner*—Fiona T. Powers
(74) *Attorney, Agent, or Firm*—Foley Hoag, LLP

(57) ABSTRACT

Compounds of the formula (I) are disclosed which are FabI inhibitors and are useful in the treatment of bacterial infections.

9 Claims, No Drawings

SEQUENCE LISTING

<160> NUMBER OF SEQ ID NOS: 4

<210> SEQ ID NO 1
<211> LENGTH: 39
<212> TYPE: DNA
<213> ORGANISM: Home sapiens

<400> SEQUENCE: 1
cgcctcgaga tgttaaatct tgaaaacaaa acatatgtc       39

-continued

```
<210> SEQ ID NO 2
<211> LENGTH: 33
<212> TYPE: DNA
<213> ORGANISM: Homo sapiens

<400> SEQUENCE: 2
cgcggatcca atcaagtcag gttgaaatat cca                              33

<210> SEQ ID NO 3
<211> LENGTH: 28
<212> TYPE: DNA
<213> ORGANISM: Home sapiens

<400> SEQUENCE: 3
catgggctta aatcttgaaa acaaaaca                                    28

<210> SEQ ID NO 4
<211> LENGTH: 26
<212> TYPE: DNA
<213> ORGANISM: Home sapiens

<400> SEQUENCE: 4
tatgttttgt tttcaagatt taagcc                                      26
```

FAB I INHIBITORS

This application claims the benefit of Provisional application No. 60/258,529, filed Oct. 8, 1999.

FIELD OF THE INVENTION

This invention relates to pharmaceutically active compounds which inhibit FabI and are useful for the treatment of bacterial infections.

BACKGROUND OF THE INVENTION

While the overall pathway of saturated fatty acid biosynthesis is similar in all organisms, the fatty acid synthase (FAS) systems vary considerably with respect to their structural organization. Vertebrates and yeast possess a FAS in which all the enzymatic activities are encoded on one or two polypeptide chains, respectively, and the acyl carrier protein (ACP) is an integral part of the complex. In contrast, in bacterial FAS, each of the reactions is catalyzed by a distinct, mono-functional enzyme and the ACP is a discrete protein. Therefore, there is considerable potential for the selective inhibition of the bacterial system by antibacterial agents.

FabI (previously designated EnvM) functions as an enoyl-ACP reductase (Bergler, et al, (1994), *J. Biol. Chem.* 269, 5493–5496) in the final step of the four reactions involved in each cycle of bacterial fatty acid biosynthesis. In this pathway, the first step is catalyzed by β-ketoacyl-ACP synthase, which condenses malonyl-ACP with acetyl-CoA (FabH, synthase III). In subsequent rounds, malonyl-ACP is condensed with the growing-chain acyl-ACP (FabB and FabF, synthases I and II, respectively). The second step in the elongation cycle is ketoester reduction by NADPH-dependent β-ketoacyl-ACP reductase (FabG). Subsequent dehydration by β-hydroxyacyl-ACP dehydrase (either FabA or FabZ) leads to trans-2-enoyl-ACP, which in turn is converted to acyl-ACP by NADH-dependent enoyl-ACP reductase (FabI). Further rounds of this cycle, adding two carbon atoms per cycle, eventually lead to palmitoyl-ACP (16C), where upon the cycle is stopped largely due to feedback inhibition of FabI by palmitoyl-ACP (Heath, et al, (1996), *J. Biol. Chem.* 271, 1833–1836). Thus, FabI is a major biosynthetic enzyme and is a key regulatory point in the overall synthetic pathway of bacterial fatty acid biosynthesis. Therefore, FabI is an ideal target for antibacterial intervention.

Studies have shown that diazaborine antibiotics inhibit fatty acid, phospholipid and lipopolysaccharide (LPS) biosynthesis and that the antibacterial target of these compounds is FabI. For example, derivative 2b18 from Grassberger, et al (1984) *J. Med Chem* 27 947–953 has been reported to be a non-competitive inhibitor of FabI (Bergler, et al, (1994), *J. Biol. Chem.* 269. 5493–5496). Also, plasmids containing the FabI gene from diazaborine resistant *S. typhimurium* conferred diazaborine resistance in *E. coli* (Turnowsky, et al, 1989), *J. Bacteriol.*, 171, 6555–6565). Furthermore, inhibition of FabI either by diazaborine or by raising the temperature in a FabI temperature sensitive mutant is lethal. these results demonstrate that FabI is essential to the survival of the organism (Bergler, et al, (1994), *J. Biol. Chem.* 269, 5493–5496).

Recent studies have shown that FabI is also the target for the broad spectrum antibacterial agent triclosan (McMurry, et al, (1998) *Nature* 394, 531–532). A crystal structure of the *E. coli* FabI complexed with NAD and triclosan shows that triclosan acts as a site-directed, very potent inhibitor of FabI by mimicking its natural substrate (Levy, et al, (1999) *Nature* 398, 383–384). Ward, et al ((1999) *Biochem.* 38, 12514–12525) have shown that there is no evidence for the formation of a covalent complex between FabI and triclosan, which would be analogous to the diazaborines; triclosan differs from these compounds in that it is a reversible inhibitor of FabI. The structural data for the complex of FabI with NAD and triclosan provides important information about FabI as a therapeutic target.

Importantly, it has now been discovered that certain compounds are FabI inhibitors and have antibacterial activity, and, therefore, may be useful for the treatment of bacterial infections in mammals, particularly in man.

SUMMARY OF THE INVENTION

This invention comprises compounds of the formula (I), as described hereinafter, which inhibit FabI and are useful in the treatment of bacterial infections.

This invention is also a pharmaceutical composition comprising a compound according to formula (I) and a pharmaceutically acceptable carrier.

This invention is also a method of treating bacterial infections by inhibiting FabI. In a particular aspect, the compounds of this invention are useful as antibacterial agents.

DETAILED DESCRIPTION

This invention comprises compounds of formula (I):

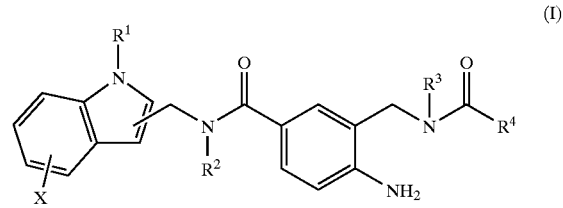

wherein:
$R^1$ is $C_{1-4}$alkyl;
$R^2$ is $C_{1-4}$alkyl;
$R^3$ is —$C_{1-4}$alkyl, —$C_{0-4}$alkyl-Ar or —$C_{0-4}$alkyl-Het;
$R^4$ is —$C_{1-4}$alkyl, —$(CH_2)_{1-4}$OH, —$OC_{1-4}$alkyl, —$SC_{1-4}$alkyl, —$N(C_{1-4}$alkyl$)_2$, —$C_{0-4}$alkyl-Ar, —$C_{0-4}$alkyl-Het, —$C_{0-4}$alkyl-$C_{3-6}$cycloalkyl, —CH(OH)—$CH_2$—R* or —$(CH_2)_{1-3}SO_2$Ar;
R* is $C_{1-4}$alkyl, Ar or Het:
X is H, $C_{1-4}$alkyl, OR', SR', CN, N(R')$_2$, $CH_2$N(R')$_2$, $NO_2$, $CF_3$, $CO_2$R', CON(R')$_2$, COR', NR'C(O)R', F, Cl, Br, I, or —S(O)$_r$CF$_3$;
R' is H, $C_{1-6}$alkyl or —$C_{0-6}$alkyl-Ar; and
r is 0, 1 or 2;
or a pharmaceutically acceptable salt thereof.

Also included in this invention are pharmaceutically acceptable addition salts and complexes of the compounds of this invention. In cases wherein the compounds of this invention may have one or more chiral centers, unless specified, this invention includes each unique racemic compound, as well as each unique nonracemic compound.

In cases in which compounds have unsaturated carbon-carbon double bonds, both the cis (Z) and trans (E) isomers are within the scope of this invention. In cases wherein compounds may exist in tautomeric forms, such as keto-enol tautomers, such as

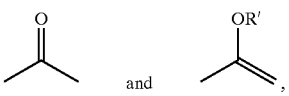
and, each tautomeric form is contemplated as being included within this invention, whether existing in equilibrium or locked in one form by appropriate substitution with R'. The meaning of any substituent at any one occurrence is independent of its meaning, or any other substituent's meaning, at any other occurrence.

Also included in this invention are prodrugs of the compounds of this invention. Prodrugs are considered to be any covalently bonded carriers which release the active parent drug according to formula (I) in vivo.

The compounds of formula (I) inhibit FabI. Inhibition of this enzyme is useful in the treatment of bacterial infections. Also, the compounds of this invention may be useful as antifungal agents. Additionally, the compounds may be useful in combination with known antibiotics.

With respect to formula (I), this invention preferably includes compounds of formula (Ia):

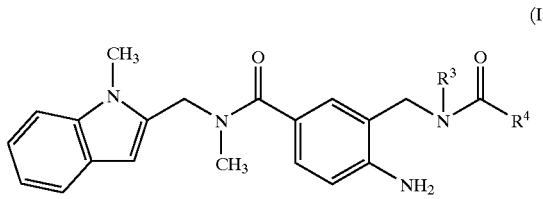
(Ia)

in which $R^3$ and $R^4$ are as defined for formula (I) compounds.

Suitably, with respect to formula (I), $R^3$ is —$C_{1-4}$alkyl or —$C_{0-2}$alkyl-Ph and $R^4$ is —$C_{1-4}$alkyl, —$CH_2OH$, —$OC_{1-4}$ alkyl, —$C_{0-2}$alkyl-Ph, —$C_{0-2}$alkyl-$C_{3-6}$cycloalkyl, —CH(OH)—$CH_2$—R* or —$(CH_2)_2SO_2Ph$, in which R* is as defined for formula (I) compounds.

Representative of the novel compounds of this invention are the following:

N-[(2-amino-5-{N-methyl-N-[(1-methylindol-2-yl)methyl]carbamoyl}phenyl)methyl]-N-methylacetamide;

N-[(2-amino-5-{N-methyl-N-[(1-methylindol-2-yl)methyl]carbamoyl}phenyl)methyl]-N-(2-phenylethyl)acetamide;

N-[(2-amino-5-{N-methyl-N-[(1-methylindol-2-yl)methyl]carbamoyl}phenyl)methyl]-2-hydroxy-4-methyl-N-methylpentanamide;

{4-amino-3-[(ethoxy-N-methylcarbonylamino)methyl]phenyl}-N-methyl-N-[(1-methylindol-2-yl)methyl]carboxamide;

N-[(2-amino-5-{N-methyl-N-[(1-methylindol-2-yl)methyl]carbamoyl}phenyl)methyl]-2-hydroxy-N-methylacetamide:

N-[(2-amino-5-{N-methyl-N-[(1-methylindol-3-yl)methyl]carbamoyl}phenyl)methyl]-N-methylacetamide;

N-[(2-amino-5-{N-methyl-N-[(1-methylindol-2-yl)methyl]carbamoyl}phenyl)methyl]-N-phenylacetamide;

N-[(2-amino-5-{N-methyl-N-[(1-methylindol-2-yl)methyl]carbamoyl}phenyl)methyl]-2-hydroxy-3-indol-3-yl-N-methylpropanamide;

(4-amino-3-{[(4-hydroxyphenyl)-N-methylcarbonylamino]methyl}phenyl)-N-methyl-N-[(1-methylindol-2-yl)methyl]carboxamide;

N-[(2-amino-5-{N-methyl-N-[(1-methylindol-2-yl)methyl]carbamoyl}phenyl)methyl]-N-methyl-3-(phenylsulfonyl)propanamide; and N-[(2-amino-5-{N-methyl-N-[(1-methylindol-2-yl)methyl]carbamoyl}phenyl)methyl]-2-cyclopentyl-N-methylacetamide;

or a pharmaceutically acceptable salt thereof.

Abbreviations and symbols commonly used in the peptide and chemical arts are used herein to describe the compounds of this invention. In general, the amino acid abbreviations follow the IUPAC-IUB Joint Commission on Biochemical Nomenclature as described in *Eur. J. Biochem.*, 158, 9 (1984).

$C_{1-4}$alkyl as applied herein means an optionally substituted alkyl group of 1 to 4 carbon atoms, and includes methyl, ethyl, n-propyl, isopropyl, n-butyl, isobutyl and t-butyl, $C_{1-6}$alkyl additionally includes pentyl, n-pentyl, isopentyl, neopentyl and hexyl and the simple aliphatic isomers thereof, $C_{0-4}$alkyl and $C_{0-6}$alkyl additionally indicates that no alkyl group need be present (e.g., that a covalent bond is present).

Any $C_{1-4}$alkyl or $C_{1-6}$ alkyl may be optionally substituted with the group $R^x$, which may be on any carbon atom that results in a stable structure and is available by conventional synthetic techniques. Suitable groups for $R^x$ are $C_{1-4}$alkyl, OR', SR', CN, N(R')$_2$, $CH_2N(R')_2$, —$NO_2$, —$CF_3$, —$CO_2R'$—CON(R')$_2$, —COR', —NR'C(O)R', F, Cl, Br, I, or —$S(O)_rCF_3$, wherein R' and r are as defined for formula (I) compounds.

Halogen or halo means F, Cl, Br, and I.

Ar, or aryl, as applied herein, means phenyl or naphthyl, or phenyl or naphthyl substituted by one to three substituents, such as those defined above for alkyl, or substituted by methylenedioxy.

Het, or heterocycle, indicates an optionally substituted five or six membered monocyclic ring, or a nine or ten-membered bicyclic ring containing one to three heteroatoms chosen from the group of nitrogen, oxygen and sulfur, which are stable and available by conventional chemical synthesis. Illustrative heterocycles are benzofuryl, benzimidazolyl, benzopyranyl, benzothienyl, furyl, imidazolyl, indolinyl, morpholinyl, piperidinyl, piperazinyl, pyrrolyl, pyrrolidinyl, tetrahydropyridinyl, pyridinyl, thiazolyl, thienyl, quinolinyl, isoquinolinyl, and tetra- and perhydro-quinolinyl and iso-quinolinyl. Any accessible combination of up to three substituents on the Het ring, such as those defined above for alkyl, that are available by chemical synthesis and are stable are within the scope of this invention.

Certain radical groups are abbreviated herein. t-Bu refers to the tertiary butyl radical, Boc refers to the t-butyloxycarbonyl radical. Fmoc refers to the fluorenylmethoxycarbonyl radical, Ph refers to the phenyl radical, Cbz refers to the benzyloxycarbonyl radical. Bn refers to the benzyl radical, Me refers to methyl, Et refers to ethyl, Ac refers to acetyl, Alk refers to $C_{1-4}$alkyl, Nph refers to 1- or 2-naphthyl and cHex refers to cyclohexyl. Tet refers to 5-tetrazolyl.

Certain reagents are abbreviated herein. DCC refers to dicyclohexylcarbodiimide. DMAP refers to dimethylaminopyridine, EDC refers to 1-(3-dimethylaminopropyl)-3-ethylcarbodiimide, hydrochloride, HOBt refers to 1-hydroxybenzotriazole, THF refers to tetrahydrofuran, DIEA refers to diisopropylethylamine, DEAD refers to diethyl azodicarboxylate, $PPh_3$ refers to triphenylphosphine, DIAD refers to diisopropyl azodicarboxylate, DME refers to dimethoxyethane, DMF refers to dimethylformamide, NBS refers to N-bromosuccinimide, Pd/C refers to a palladium on carbon catalyst, PPA refers to polyphosphoric acid, DPPA refers to diphenylphosphoryl azide, BOP refers to benzotriazol-1-yloxy-tris(dimethyl-amino)phosphonium hexafluorophosphate, HF refers to hydrofluoric acid, TEA refers to triethylamine, TFA refers to trifluoroacetic acid, PCC refers to pyridinium chlorochromate.

Generally, the compounds of formula (I) are prepared by reacting a compound of formula (II) with a compound of formula (III):

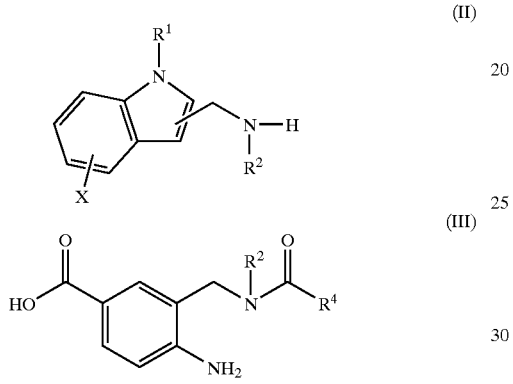

wherein $R^1$, $R^2$, $R^3$, $R^4$ and X are as defined in formula (I), with any reactive functional groups protected, in the presence of EDC and HOBT;

and thereafter removing any protecting groups, and optionally forming a pharmaceutically acceptable salt.

In particular, compounds of formula (I) are prepared by the general methods described in Scheme I.

Scheme I

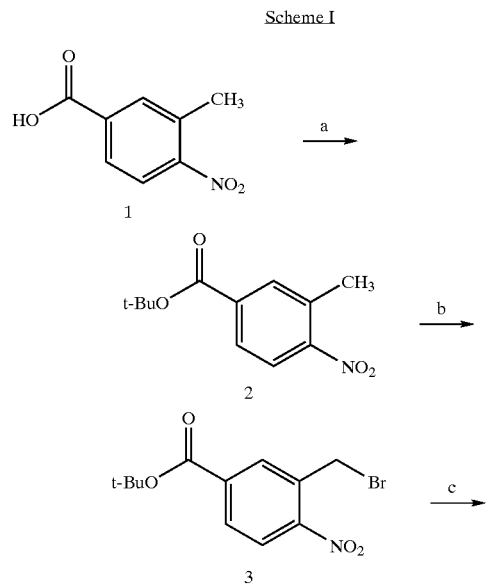

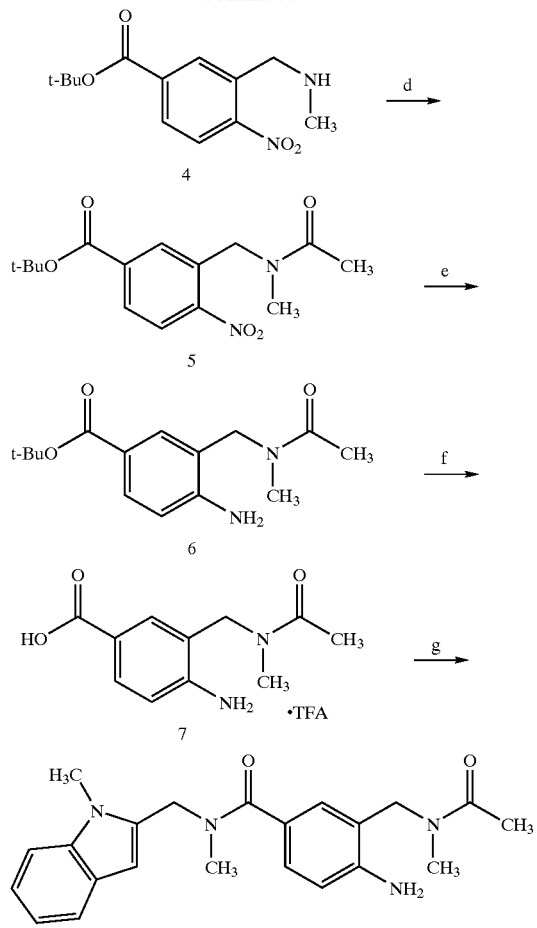

Reagents and conditions: (a) $PhSO_2Cl$, pyridine, t-BuOH; (b) N-bromosuccinamide, benzoyl peroxide, $CH_2Cl_2$; (c) 40% $CH_3NH_2$ in $H_2O$; (d) $(CH_3CO)_2O$, $(i-Pr)_2NEt$, $CH_2Cl_2$; (e) $H_2$, 10% Pd/C, MeOH; (f) TFA, $CH_2Cl_2$; (g) 1-methyl-2-(methylaminomethyl)indole, EDC, $HOBt.H_2O$. $(i-Pr)_2NEt$, DMF.

Commercially available 3-methyl-4-nitrobenzoic acid (I-1) is protected at the carboxylic acid functionality with a suitable protecting group, for instance a tertiary butyl (t-Bu) group, to afford I-2. The use of protecting groups to mask reactive functionality is well-known to those of skill in the art, and other protecting groups are listed in standard reference volumes, such as Greene, "Protective Groups in Organic Synthesis" (published by Wiley-Interscience). The benzylic position is brominated under radical conditions using N-bromosuccinamide (NBS) and the radical initiator benzoyl peroxide affording I-3. Halogenation of reactive positions, such as the benzylic position of I-2, is well known. Nucleophilic substitution of the bromide is accomplished with an excess of aqueous methyl amine, for instance 40% methylamine in water, providing the benzyl amine I-4. Acylation of the pendent nitrogen is accomplished with a suitable acylating reagent such as an acyl halide, or an acid anhydride, to afford N-acyl-substituted derivatives. For example, the benzyl nitrogen can be acylated with acetic anhydride, to afford the amide derivative I-5. The aryl nitro compound I-5 is converted under hydrogenation conditions, in the presence of a catalytic amount of palladium metal on activated carbon (Pd/C), to the amine I-6. Aromatic nitro groups can be reduced by a number of methods involving the use of metals and example procedures can be found in standard chemistry texts such as, "Reductions in Organic Chemistry" published by the (American Chemical Society). The t-butyl ester is removed to reveal the carboxylic acid functionality with a suitable acid reagent such as trifluoroacetic acid (TFA) to give I-7. Other standard methods for removal of a t-butyl protecting group are described by Greene (see above). The carboxylic acid derivative is then converted to amide I-8 by reaction with an activating agent and a suitable amine species. For example, acid I-7 is converted to an activated form by reaction with EDC and HOBt, and the activated form is subsequently reacted with amine [1-methyl-2-(methylaminomethyl)indole] in a suitable solvent such as DMF, $CH_2Cl_2$, or $CH_3CN$. Depending on whether acid neutralization is required, an added base, such as triethylamine ($Et_3N$), diisopropylethylamine ($(i-Pr)_2NEt$), or pyridine, may be used.

Many additional methods for converting a carboxylic acid to an amide are known, and can be found in standard reference books, such as "Compendium of Organic Synthetic Methods". Vol. I–VI (published by Wiley-Interscience), or Bodansky, "The Practice of Peptide Synthesis" (published by Springer-Verlag), which are incorporated herein by reference.

Amide coupling reagents as used herein denote reagents which may be used to form peptide bonds. Typical coupling methods employ carbodiimides, activated anhydrides and esters and acyl halides. Reagents such as EDC, DCC, DPPA, PPA, BOP reagent, HOBt, N-hydroxysuccinimide and oxalyl chloride are typical.

Typically, the amine is coupled via its free amino group to an appropriate carboxylic acid substrate using a suitable carbodiimide coupling agent, such as N,N'dicyclohexyl carbodiimide (DCC), optionally in the presence of catalysts such as 1-hydroxybenzotriazole (HOBt) and dimethylamino pyridine (DMAP). Other methods, such as the formation of activated esters, anhydrides or acid halides, of the free carboxyl of a suitably protected acid substrate, and subsequent reaction with the free amine, optionally in the presence of a base, are also suitable. For example, a benzoic acid is treated in an anhydrous solvent, such as methylene chloride or tetrahydrofuran (THF), in the presence of a base, such as N-methylmorpholine, DMAP or a trialkylamine, with isobutyl chloroformate to form the "activated anhydride", which is subsequently reacted with the free amine.

Acid addition salts of the compounds are prepared in a standard manner in a suitable solvent from the parent compound and an excess of an acid, such as hydrochloric, hydrobromic, hydrofluoric, sulfuric, phosphoric, acetic, trifluoroacetic, maleic, succinic or methanesulfonic. Certain of the compounds form inner salts or zwitterions which may be acceptable. Cationic salts are prepared by treating the parent compound with an excess of an alkaline reagent, such as a hydroxide, carbonate or alkoxide, containing the appropriate cation; or with an appropriate organic amine. Cations such as $Li^+$, $Na^+$, $K^+$, $Ca^{++}$, $Mg^{++}$ and $NH_4^+$ are specific examples of cations present in pharmaceutically acceptable salts.

This invention also provides a pharmaceutical composition which comprises a compound according to formula (I) and a pharmaceutically acceptable carrier. Accordingly, the compounds of formula (I) may be used in the manufacture of a medicament. Pharmaceutical compositions of the compounds of formula (I) prepared as hereinbefore described may be formulated as solutions or lyophilized powders for parenteral administration. Powders may be reconstituted by addition of a suitable diluent or other pharmaceutically acceptable carrier prior to use. The liquid formulation may be a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride or sodium citrate.

Alternately, these compounds may be encapsulated, tableted or prepared in a emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

For rectal administration, the compounds of this invention may also be combined with excipients, such as cocoa butter, glycerin, gelatin or polyethylene glycols, and molded into a suppository.

For topical administration, the compounds of this invention may be combined with diluents to take the form of ointments, gels, pastes, creams, powders or sprays. The compositions which are ointments, gels, pastes or creams contain diluents, for example animal and vegetable fats, waxes, paraffins, starch, tragacanth, cellulose derivatives, polyethylene glycols, silicones, bentonites, silicic acid, talc and zinc oxide, or mixtures of these substances. The compositions which are powders or sprays contain diluents, for example, lactose, talc, silicic acid, aluminum hydroxide, calcium silicate and polyamide powder, or mixtures of these substances. Additionally, for topical ophthalmologic administration, the typical carriers are water, mixtures of water and water miscible solvents, such as lower alkanols or vegetable oils, and water-soluble non-toxic polymers, for example cellulose derivatives, such as methyl cellulose.

The compounds described herein are inhibitors of FabI, and are useful for treating bacterial infections. For instance, these compounds are useful for the treatment of bacterial infections, such as, for example, infections of upper respiratory tract (e.g. otitis media, bacterial tracheitis, acute epiglottitis, thyroiditis), lower respiratory (e.g. empyema, lung abscess), cardiac (e.g. infective endocarditis), gastrointestinal (e.g. secretory diarrhoea, splenic abscess, retroperitoneal abscess), CNS (e.g. cerebral abscess), eye (e.g. blepharitis, conjunctivitis, keratitis, endophthalmitis, preseptal and orbital cellulitis, darcryocystitis), kidney and urinary tract (e.g. epididymitis, intrarenal and perinephric abscess, toxic shock syndrome), skin (e.g. impetigo, folliculitis, cutaneous abscesses, cellulitis, wound infection, bacterial myositis), and bone and joint (e.g. septic arthritis, osteomyelitis). Also, the compounds of this invention may be useful as antifungal agents. Additionally, the compounds may be useful in combination with known antibiotics.

The compounds of this invention are administered to the patient, in a manner such that the concentration of drug is sufficient to treat bacterial infections. The pharmaceutical composition containing the compound is administered at an oral dose of between about 10 mg to about 1000 mg, taken once or several times daily, in a manner consistent with the condition of the patient. Preferably, the oral dose would be about 50 mg to about 500 mg, although the dose may be varied depending upon the age, body weight and symptoms of the patient. For acute therapy, parenteral administration is preferred. An intravenous infusion of the compound of formula (I) in 5% dextrose in water or normal saline, or a similar formulation with suitable excipients, is most effective, although an intramuscular bolus injection is also useful. The precise level and method by which the compounds are administered is readily determined by one skilled in the art.

The compounds may be tested in one of several biological assays to determine the concentration of compound which is required to have a given pharmacological effect.

Cloning of S. aureus FabI:

The fabI gene was cloned from the chromosomal DNA of S. aureus strain WCUH29 using the polymerase chain reaction. Amplification was performed using Taq DNA polymerase (BRL) and the following primers: 5'-CGC CTCGAGATGTTAAATCTTGAAAACAAAACATATG TC-3' and 5'-CGCGGATCCAATCAAGTCAGGTT GAA ATATCCA-3' (XhoI and BamHI sites underlined). The resulting fragment was then digested with XhoI and BamHI and ligated into XhoI- and BamHI-digested expression vector pET-16b (Novagen), producing pET-His$_{10}$-fabI. The gene sequence of fabI was confirmed by automated cycle sequencing using an Applied Biosystems model 377 machine. The untagged version of pET-fabI was constructed by digesting pET-His$_{10}$-fabI with NcoI and NdeI to remove a 97 bp fragment encoding the His 10 tag, the factor Xa cleavage site and the first 8 amino acids of FabI, and replacing it with a linker encoding the first 8 amino acids of FabI plus a glycine residue between the initiator methionine and the lysine at position 2. This plasmid was called pET-fabI. The linker was made by annealing the following two oligonucleotides: 5'-CATGGGCTTAAATCT TGAAAACAAAACA-3' and 5'-TATGTTTTGTTTTCA TTTAAGCC-3'. The linker sequence in pET-fabI was confirmed by dideoxy sequencing. Only native FabI was used for compound evaluation. For overproduction of native FabI, plasmid pET-fabI was transformed into BL21(DE3) (Novagen) cells, to form strain BL21(DE3):pET-fabI.

Purification of S. aureus FabI

S. aureus FabI was expressed as soluble protein to 10% of total cell protein, 400 g cells being recovered from 15 L fermentation in tryptone phosphate medium. The cells were lysed and the sample centrifuged. The resulting supernatant was filtered and purified using three consecutive chromatography columns: ion-exchange (Sourse 15Q), dye-affinity (Blue sepharose), and size exclusion chromatography columns (Superose 12). After each column the FabI containing fractions were pooled, concentrated, and checked for purity and biological activity.

Cloning of E. coli FabI:

A PCR fragment of correct size for E. coli FabI was PCR amplified from E. coli chromosomal DNA. subcloned into the TOPO TA cloning vector, and verified by colony PCR+ restriction endonuclease analysis. The presumptive E. coli FabI PCR fragment was subcloned into the expression vector pBluePet. The FabI clone was transformed into E. coli strain BL21(DE3). Small Scale expression studies show an over-expressed protein band of correct molecular weight (~28 Kda) for E. coli FabI clearly visible following Coomassie staining of SDS PAGE gels. DNA sequencing of the E. coli FabI expression constructs illustrated that no errors were apparent. N' terminal amino acid sequencing has confirmed the over-expressed protein band to be E. coli FabI.

Purification of E. coli FabI

E. coli FabI was expressed as soluble protein to 15% of total cell protein, 120 g cells being recovered from 3 L fermentation in shake flasks in modified terrific broth. The cells were lysed and the sample centrifuged. The resulting supernatant was filtered and purified using three consecutive chromatography columns: ion-exchange (Sourse 15Q), dye-affinity (blue sepharose), and size exclusion (superose 12). After each column the FabI containing fractions were pooled, concentrated and checked for purity and biological activity.

S. aureus FabI Enzyme Inhibition Assay (NADH):

Assays were carried out in half-area, 96-well microtitre plates. Compounds were evaluated in 50-uL assay mixtures containing 100 mM NaADA, pH 6.5 (ADA=N-[2-acetamido]-2-iminodiacetic acid), 4% glycerol, 0.25 mM crotonoyl CoA, 1 mM NADH, and an appropriate dilution of S. aureus FabI. Inhibitors were typically varied over the range of 0.01–10 uM. The consumption of NADH was monitored for 20 minutes at 30° C. by following the change in absorbance at 340 nm. Initial velocities were estimated from an exponential fit of the non-linear progress curves represented by the slope of the tangent at t=0 min. IC$_{50}$'s were estimated from a fit of the initial velocities to a standard, 4-parameter model and are typically reported as the mean±S.D. of duplicate determinations. Triclosan, a commercial antibacterial agent and inhibitor of FabI, is currently included in all assays as a positive control. Compounds of this invention have IC$_{50}$'s from about 2.0 micromolar to about 0.15 micromolar.

S. aureus FabI Enzyme Inhibition Assay (NADPH):

Assays were carried out in half-area, 96-well microtitre plates. Compounds were evaluated in 150-uL assay mixtures containing 100 mM NaADA, pH 6.5 (ADA=N-[2-acetamido]-2-iminodiacetic acid), 4% glycerol, 0.25 mM crotonoyl CoA, 50 uM NADPH, and an appropriate dilution of S. aureus FabI. Inhibitors were typically varied over the range of 0.01–10 uM. The consumption of NADPH was monitored for 20 minutes at 30° C. by following the change in absorbance at 340 nm. Initial velocities were estimated from an exponential fit of the non-linear progress curves represented by the slope of the tangent at t=0 min. IC$_{50}$'s were estimated from a fit of the initial velocities to a standard, 4-parameter model and are typically reported as the mean±S.D. of duplicate determinations. Triclosan, a commercial antibacterial agent and inhibitor of FabI, is currently included in all assays as a positive control.

E. coli FabI Enzyme Inhibition Assay:

Assays were carried out in half-area, 96-well microtitre plates. Compounds were evaluated in 150-uL assay mixtures containing 100 mM NaADA, pH 6.5 (ADA=N-[2-acetamido]-2-iminodiacetic acid), 4% glycerol, 0.25 mM crotonoyl CoA, 50 uM NADH, and an appropriate dilution of E. coli FabI. Inhibitors were typically varied over the range of 0.01–10 uM. The consumption of NADH was monitored for 20 minutes at 30° C. by following the change in absorbance at 340 nm. Initial velocities were estimated from an exponential fit of the non-linear progress curves represented by the slope of the tangent at t=0 min. $IC_{50}$'s were estimated from a fit of the initial velocities to a standard, 4-parameter model and are typically reported as the mean±S.D. of duplicate determinations. Triclosan, a commercial antibacterial agent and inhibitor of FabI, is currently included in all assays as a positive control. Compounds of this invention have $IC_{50}$'s from about 4.0 micromolar to about 0.15 micromolar.

Preparation and Purification of Crotonoyl-ACP:

Reactions contained 5 mg/mL E. coli apo-ACP, 0.8 mM crotonoyl-CoA (Fluka), 10 mM $MgCl_2$, and 30 uM S. pneumoniae ACP synthase in 50 mM NaHEPES, pH 7.5. The mixture was gently mixed on a magnetic stirrer at 23° C. for 2 hr, and the reaction was terminated by the addition of 15 mM EDTA. The reaction mixture was filtered through a 0.2 micron filter (Millipore) and applied to a MonoQ column (Pharmacia) equilibrated with 20 mM Tris-Cl, pH 7.5. The column was washed with buffer until all non-adherent material was removed (as observed by UV detection), and the crotonoyl-ACP was eluted with a linear gradient of 0 to 400 mM NaCl.

S. aureus FabI Enzyme Inhibition Assay Using Crotonoyl-ACP:

Assays are carried out in half-area, 96-well microtitre plates. Compounds are evaluated in 150 uL assay mixtures containing 100 mM NaADA, pH 6.5 (ADA=N-(2-acetamido)-2-iminodiacetic acid), 4% glycerol, 25 uM crotonoyl-ACP, 50 uM NADPH, and an appropriate dilution of S. aureus FabI (approximately 20 nM). Inhibitors are typically varied over the range of 0.01–10 uM. The consumption of NADPH is monitored for 20 minutes at 30° C. by following the change in absorbance at 340 nm. Initial velocities are estimated from a linear fit of the progress curves. IC50's are estimated from a fit of the initial velocities to a standard, 4-parameter model (Equation 1) and are typically reported as the mean±S.D. of duplicate determinations. The apparent Ki is calculated from Equation assuming the inhibition is competitive with crotonoyl-ACP.

v=Range/(1+[I]/IC50)s+Background     Equation 1:

Ki(app)=IC50/(1+[S]/Ks)     Equation 2:

Antimicrobial Activity Assay:

Whole-cell antimicrobial activity was determined by broth microdilution using the National Committee for Clinical Laboratory Standards (NCCLS) recommended procedure, Document M7-A4, "Methods for Dilution Susceptibility Tests for Bacteria that Grow Aerobically". The compound was tested in serial two-fold dilutions ranging from 0.06 to 64 mcg/mL. Test organisms were selected from the following laboratory strains:

Staphylococcus aureusOxford Staphylococcus aureus WCUH29, Streptococcus pneumoniae ERY2, Streptococcus pneumoniae 1629, Streptococcus pneumoniae N 1387, Enterococcus faecalis 1, Enterococcus faecalis 7, Haemophilus influenzae Q1, Haemophilus influenzae NEMCI, Moraxella Catarrhalis 1502, Escherichia coli 7623 AcrABEFD+, Escherichia coli 120 AcrAB−, Escherichia coli MG1655, Escherichia coli MG1658. The minimum inhibitory concentration (MIC) was determined as the lowest concentration of compound that inhibited visible growth. A mirror reader was used to assist in determining the MIC endpoint.

One skilled in the art would consider any compound with a MIC of less than 256 µg/mL to be a potential lead compound. Preferably, the compounds used in the antimicrobial assays of the present invention have a MIC value of less than 128 µg/mL. Most preferably, said compounds have a MIC value of less than 64 µg/mL.

The examples which follow are intended in no way to limit the scope of this invention, but are provided to illustrate how to make and use the compounds of this invention. Many other embodiments will be readily apparent to those skilled in the art.

EXAMPLES

General

Proton nuclear magnetic resonance ($^1$H NMR) spectra were recorded at 300 MHz, and chemical shifts are reported in parts per million (δ) downfield from the internal standard tetramethylsilane (TMS). Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. $CDCl_3$ is deuteriochloroform, DMSO-$d_6$ is hexadeuteriodimethylsulfoxide, and $CD_3OD$ is tetradeuteriomethanol. Mass spectra were obtained using electrospray (ES) ionization techniques. Elemental analyses were performed by Quantitative Technologies Inc., Whitehouse, N.J. Melting points were obtained on a Thomas-Hoover melting point apparatus and are uncorrected. All temperatures are reported in degrees Celsius. Analtech Silica Gel GF and E. Merck Silica Gel 60 F-254 thin layer plates were used for thin layer chromatography. Flash chromatography was carried out on E. Merck Kieselgel 60 (230–400 mesh) silica gel. Analytical HPLC was performed on Beckman chromatography systems. Preparative HPLC was performed using Gilson chromatography systems. ODS refers to an octadecylsilyl derivatized silica gel chromatographic support. YMC ODS-AQ® is an ODS chromatographic support and is a registered trademark of YMC Co. Ltd., Kyoto, Japan. PRP-1® is a polymeric (styrene-divinylbenzene) chromatographic support, and is a registered trademark of Hamilton Co., Reno, Nev. Celite® is a filter aid composed of acid-washed diatomaceous silica, and is a registered trademark of Manville Corp., Denver, Colo.

Preparation 1

Preparation of 1-methyl-2-(methylaminomethyl)indole a) Ethyl 1-methylindole-2-carboxylate NaH (60% dispersion in mineral oil, 8.0 g, 200.5 mmole) was washed with hexanes, then was suspended in dry DMF (530 mL). Solid ethyl indole-2-carboxylate (25.3 g, 133.7 mmole) was added portionwise over 5–10 min, allowing gas evolution to subside between additions. When the addition was complete, the yellow mixture was stirred for 15 min, then methyl iodide (42 mL, 668.3 mmole) was added all at once. The reaction was exothermic, and the internal temperature rose to 40–45° C. After 1 hr, the reaction was quenched with 10% $NH_4Cl$ (100 mL) and concentrated on the rotavap (high vacuum). The residue was partitioned between $Et_2O$ (500 mL) and $H_2O$ (100 mL), and the layers were separated. The $Et_2O$ layer was washed with $H_2O$ (100 mL). dried ($MgSO_4$), and concentrated to leave the title compound (27.1 g, quantitative) as a light yellow solid. This was used without further purification: TLC (10% EtOAc/hexanes) $R_f$=0.39.

b) N,1-Dimethylindole-2-carboxamide

A suspension of ethyl 1-methylindole-2-carboxylate (27.1 g, 133.3 mmole) in 40% aqueous $CH_3NH_2$ (300 mL) and MeOH (30 mL) was stirred at RT. A solid tended to gradually creep up the walls of the flask, and was washed down periodically with MeOH. The flask was tightly stoppered to keep the material inside the flask. As the reaction proceeded, the solid dissolved, but eventually the product began to precipitate. The reaction was stirred at RT for 3 days, then was concentrated to remove approximately 200 mL of the solvent. The remaining residue was diluted with $H_2O$ (300 mL), and the solid was collected by suction filtration and washed with $H_2O$. Drying at 50–60° C. in high vacuum left the title compound (23.4 g, 93%) as a faintly yellow solid: MS (ES) m/e 189 (M+H)$^+$.

c) 1-Methyl-2-(methylaminomethyl)indole

A 3-liter 3-necked roundbottom flask equipped with overhead stirring was charged with N,1-dimethylindole-2-carboxamide (23.4 g, 124.6 mmole) and anhydrous THF (170 mL). The solution was stirred while a solution of $LiAlH_4$ in THF (1.0 M, 250 mL, 250 mmole) was added via syringe. Gas was evolved during the addition of the first 50 mL of $LiAlH_4$ solution. When the addition was complete, the resulting light yellow solution was heated at gentle reflux. After 24 hr, the reaction was cooled in ice and quenched by the sequential dropwise addition of $H_2O$ (9.5 mL), 15% NaOH (9.5 mL), and $H_2O$ (28.5 mL).

The mixture was stirred for 15 min, then was filtered through celite®, and the filter pad was washed thoroughly with THF. The filtrate was concentrated and the residue was flash chromatographed on silica gel (10% $MeOH/CHCl_3$ containing 5% conc. $NH_4OH$). The title compound (20.2 g, 93%) was obtained as a light yellow oil: MS (EI) m/e 175 (M+H)$^+$.

Preparation 2

The Preparation of 1-Methyl-3-(methylaminomethyl)indole a) Ethyl 1-methylindole-3-carboxylate According to the procedure of Preparation 1a, except substituting ethyl 3-indole acetate (25.3 g, 133.7 mmole) for ethyl indole-2-carboxylate, the title compound was prepared as a light yellow solid and used without further purification.

b) N,1-Dimethylindole-3-carboxamide

According to the procedure of Preparation 1b, except substituting ethyl 1-methylindole-3-carboxylate (27.1 g, 133.3 mmole) for ethyl 1-methylindole-2-carboxylate, the title compound (23.4 g, 93%) was prepared as a light yellow solid and used without further purification: MS (ES) m/e 189 (M+H)$^+$.

c) 1-Methyl-3-(methylaminomethyl)indole

According to the procedure of Preparation 1c, except substituting N,1-dimethylindole-3-carboxamide (23.4 g, 124.6 mmole) for N,1-dimethylindole-2-carboxamide, the title compound (20.2 g, 93%) was prepared as a light yellow oil: MS (ES) m/e 175 (M+H)$^+$.

Preparation 3

Preparation of 4-amino-3-[(N-methylacetylamino)methyl] benzoic acid trifluoroacetate a) tert-Butyl 3-methyl-4-nitro benzoate To a pyridine solution of 3-methyl-4-nitrobenzoic acid (18.1 g, 100.0 mmole) at RT was added benzenesulfonyl chloride in one portion. After 10 min. anhydrous t-butanol (9.4 mL, 100.0 mmole) was added and the reaction solution was allowed to stir for 1 hr. The resulting suspension was poured into ice-water (400 mL) and stirred vigorously for 1 hr. The light yellow suspension was filtered through a scinter-glass funnel washing with $H_2O$. The remaining yellow solids were dissolved in toluene (400 mL), dried over $MgSO_4$ and then filtered through a short column of silica gel washing with toluene. Concentration of the solution under vacuum (15 mm Hg) and drying on high vacuum afforded the tide compound (22.5 g, 95%) as a light yellow solid: MS (ES) m/e 238 (M+H)$^+$.

b) tert-Butyl 3-methylaminomethyl-4-nitro benzoate

To a stirred solution of tert-butyl 3-methyl-4-nitro benzoate (22.5 g, 94.9 mmole) in $CH_2Cl_2$ (450 mL) at RT contained in a 1 L one-neck round bottom flask was added NBS (18.6 g, 104.4 mmole) and benzoyl peroxide (2.3 g, 9.5 mmole). The flask was equipped with a reflux condenser and a 150 watt tungsten-light source was shined on the reaction for 36 hrs. The reaction solution was washed with $H_2O$, dried over $Na_2SO_4$ and concentrated under vacuum. The resulting orange residue was dissolved in ethyl acetate and filtered through silica gel (EtOAc/hexanes, 1:4). Concentration on a rotary evaporator gave an orange oil which was used directly in the next step without further purification.

To the crude bromide in THF (150 mL) was added 40% aqueous $CH_3NH_2$ (50 mL) in one portion at RT. After 18 hr, the reaction solution was concentrated to remove the THF. The resulting aqueous solution was extracted with EtOAc (2×200 mL) and the combined organic phases were sequentially washed with $H_2O$ and brine. Drying over $K_2CO_3$ and concentration gave a yellow oil which was purified on silica (hexanes/EtOAc, 1:1) to afford the title compound (19.2 g, 76%) as a light yellow solid: MS (ES) m/e 267 (M+H)$^+$.

c) tert-Butyl-4-amino-3-[(N-methylacetylamino)methyl] benzoate

To a stirred solution of t-butyl 3-(methylaminomethyl)-4-nitro benzoate (2.4 g, 9.0 mmole) in $CH_2Cl_2$ at RT was added $Et_3N$ (2.52 mL, 18.0 mmole) and acetic anhydride (1.8 g, 18.0 mmole). After 12 hrs. the reaction solution was concentrated under vacuum, dissolved in EtOAc (150 mL) and washed with $H_2O$. The EtOAc solution was dried over $Na_2SO_4$ and concentrated under vacuum to a yellow oil. The oil was further dried under high vacuum and used directly in the next procedure.

The crude product was dissolved in EtOAc (50 mL) and $CH_3OH$ (50 mL) and placed in a Parr hydrogenation flask. A catalytic amount of 10% Pd/C was added to the reaction solution and the contents were placed on a Parr shaker under $H_2$ (50 psi) and shaken for 4 hours. The solution was filtered through celite and concentrated under vacuum. Purification on silica (hexanes/EtOAc, 1:1) afforded the title compound (2.13 g, 85% over two steps) as an off-white solid: MS (ES) m/e 279 (M+H)$^+$.

d) 4-amino-3-[(N-methylacetylamino)methyl]benzoic acid trifluoroacetate salt

To a solution of t-butyl 4-amino-3-[(N-methylacetylamino)methyl]benzoate (2.13 g, 7.65 mmole) in $CH_2Cl_2$ (150 mL) at RT was added TFA (30 mL). After 12 hr, the reaction solution was concentrated to an oil and dried under high vacuum overnight. The resulting residue was washed with hexanes and $Et_2O$ to afford the title compound (2.56 g, 7.60 mmole) as an off-white solid. This compound was used without further purification: MS (ES) m/e 223 (M+H-TFA)$^+$.

Preparation 4

Preparation of 4-amino-3-[(N-phenethylacetylamino) methyl]benzoic acid a) tert-Butyl 4-nitro-3-(phenethylamino)methyl benzoate Crude tert-butyl 3-bromomethyl-4-nitrobenzoate (from Preparation 3b) was dissolved in dry THF (50 mL), and solid $NaHCO_3$ (2.52 g, 30 mmole) was added. The mixture was stirred briskly, and phenethylamine (3.8 mL, 30 mmole) was added. The color of the solution darkened slightly to a deeper yellow. Within several minutes, the mixture had become very cloudy. After 4 hr, the reaction was concentrated and the residue was partitioned between $H_2O$ (50 mL) and $Et_2O$ (100 mL). The layers were separated, and the aqueous layer was extracted with $Et_2O$ (2×100 mL). The organic layers were combined, dried ($MgSO_4$), and concentrated to a yellow oil. Flash chromatography on silica gel (20% EtOAc/hexanes) gave the title compound (2.86 g, 40% for two steps) as a yellow oil: $^1$H NMR (250 MHz, $CDCl_3$) δ 8.19 (d, J=1.7 Hz, 1H), 7.98 (dd, J=8.4, 1.7 Hz, 1H), 7.90 (d. J=8.4 Hz, 1H), 7.10–7.40 (m, 5H), 4.06 (s, 2H), 2.75–3.00 (m, 4H), 1.61 (s, 9H); MS (ES) m/e 357 (M+H)$^+$.

b) tert-Butyl 3-[N-(tert-butoxycarbonyl)-N-phenethylamino]methyl-4-nitrobenzoate Di-tert-butyl dicarbonate (2.10 g, 9.62 mmole) was added all at once to a solution of tert-butyl 3-(phenethylamino) methyl-4-nitrobenzoate (2.86 g, 8.02 mmole) in $CHCl_3$ (30 mL) at RT. The reaction was stirred at RT For 2.5 hr, then at reflux for 0.5 hr. Concentration and flash chromatography on silica gel (15% EtOAc/hexanes) gave the title compound (3.70 g, quantitative) as a yellow oil: $^1$H NMR (250 MHz, $CDCl_3$) δ 7.85–8.10 (m, 3H), 7.05–7.40 (m, 5H), 4.55–4.85 (m, 2H), 3.35–3.60 (m, 2H), 2.75–3.00 (m, 2H), 1.20–1.80 (m, 18H); MS (ES) m/e 479 (M+Na)$^+$, 457 (M+H)$^+$.

c) tert-Butyl 4-amino-3-[[N-(tert-butoxycarbonyl)-N-phenethylamino]methyl]benzoate A mixture of tert-butyl 3-[[N-(tert-butoxycarbonyl)-N-phenethylamino]methyl]-4-nitrobenzoate (2.7 g, 5.9 mmole), 10% Pd/C (0.6 g, 0.6 mmole Pd), and EtOAc (60 mL) was shaken under $H_2$ (50 psi). After 3 hr, the mixture was filtered to remove the catalyst, and the filtrate was concentrated to dryness. Flash chromatography on silica gel (20% EtOAc/hexanes) gave the title compound (2.3 g, 91%) as a yellow foamy oil which slowly partially solidified: $^1$H NMR (250 MHz, $CDCl_3$) δ 7.74 (dd, J=8.4, 2.0 Hz, 1H), 7.67 (d, J=2.0 Hz, 1H), 7.05–7.40 (m, 5H), 6.57 (d, J=8.4 Hz, 1H), 5.00 (br s, 2H), 4.30 (s, 2H), 3.32 (app. t, 2H), 2.69 (app. t, 2H), 1.59 (s, 9H), 1.46 (s, 9H); MS (ES) m/e 449.2 (M+Na)$^+$, 427.2 (M+H)$^+$.

d) 4-amino-3-[N-phenethylaminomethyl]benzoate trifluoroacetate salt

To a solution of tert-butyl 4-amino-3-[[N-(tert-butoxycarbonyl)-N-phenethylamino]methyl]benzoate (2.3 g, 5.4 mmole) in $CH_2Cl_2$ (100 mL) at RT was added TFA (25 mL). After 12 hr, the reaction solution was concentrated to an oil and the residue dried under high vacuum overnight. The resulting residue was washed with hexanes and diethyl ether to afford the title compound (2.7 g, 5.4 mmole) as an off-white solid: MS (ES) m/e 271 (M+H-2TFA)$^+$.

e) 4-amino-3-[(N-phenethylacetylamino)methyl]benzoic acid

To a stirred solution of 4-amino-3-[N-phenethylaminomethyl]benzoate bis-trifluoroacetate salt (1.0 g, 2.0 mmole) in $CH_2Cl_2$ at RT was added $Et_3N$ (1.1 mL, 7.9 mmole) and acetic anhydride (0.26 g, 2.6 mmole). After 12 hr, the reaction solution was concentrated under vacuum, dissolved in 1M NaOH (15 mL), and washed with hexanes. The aqueous solution was neutralized with 1M HCl and extracted with EtOAc (2×50 mL). The EtOAc solution was dried over $Na_2SO_4$ and concentrated to an off-white solid which was used without further purification: MS (ES) m/e 313 (M+H)$^+$.

Preparation 5
Preparation of tert-Butyl-4-amino-3-[(N-methyl) aminomethyl)]benzoate A solution of t-butyl-3-[N-(methyl)aminomethyl]-4-nitrobenzoate (12.0 g, 45.1 mmole), from procedure 3a, in $CH_3OH$ (50 mL) was placed in a Parr hydrogenation flask. Approximately (0.50 g) of 10% Pd/C was added to the reaction solution and the contents were shaken on a Parr shaker under $H_2$ (50 psi) for 4 hours. The suspension was filtered through celite and concentrated under vacuum. Washing of the resulting residue with $Et_2O$ afforded a viscous light yellow oil which was used without further purification: MS (ES) m/e 237 (M+H)$^+$.

Preparation 6
Preparation of 4-amino-3-[(2-hydroxy-4,N-dimethylpentanoylamino)methyl]benzoic acid trifluoroacetate a) tert-Butyl-4-amino-3-[(2-hydroxy-4,N-dimethylpentanoylamino)methyl]benzoic acid To a stirred solution of t-butyl-3-[N-(methyl) aminomethyl]-4-amino benzoate (2.6 g, 11.0 mmole) in DMF (20 mL) at RT was added diisopropylethyl amine (2.9 mL, 16.9 mmole), HOBt (2.3 g, 16.9 mmole) 2-hydroxy-4-methylpentanoic acid (2.04 g, 15.15 mmole) and finally EDC (3.24 g, 16.9 mmole). After 12 hr, the reaction contents were poured onto $H_2O$ (200 mL) and extracted with EtOAc (2×150 mL). The organic phases were combined and sequentially washed with $H_2O$ (100 mL) and brine. Drying over $Na_2SO_4$ and purification on silica ($CHCl_3/CH_3OH$, 95:5) afforded the title compound (3.50 g, 91%) as a light yellow oil: MS (ES) m/e 351 (M+H)$^+$.

b) 4-Amino-3-[(2-hydroxy-4,N-dimethylpentanoylamino)methyl]benzoic acid trifluoroacetate To a stirred solution of t-butyl-4-amino-3-[(2-hydroxy-4,N-dimethylpentanoylamino)methyl]benzoic acid (3.50 g, 10.0 mmole) in $CH_2Cl_2$ (20 mL) at RT was added TFA (20 mL). After 12 hr, the reaction contents were evaporated, washed with hexanes and dried under high vacuum overnight affording the title compound as an orange oil (4.42 g, 10.8 mmol). This product was used without further purification: MS (ES) m/de 295 (M+H-TFA)$^+$.

Preparation 7
Preparation of 4-amino-3-[(ethoxy-N-methylcarbonylamino)methyl]benzoic acid trifluoro acetate a) tert-Butyl 4-amino-3-[(ethoxy-N-methylcarbonylamino)methyl]benzoate To a stirred solution of t-butyl 3-[N-(methyl) aminomethyl]-4-amino benzoate (251 g, 10.63 mmole) in $CH_2Cl_2$ (20 mL) at 0° C. was added triethyl amine (1.63 mL, 11.7 mmole), and ethylchloroformate (1.15 g, 10.63 mmole). The reaction solution was allowed to warm to RT overnight. The reaction contents were concentrated under vacuum and partition between $H_2O$ (100 mL) and EtOAc (200 mL). The organic phase was combined washed sequentially with $H_2O$ (100 mL) and brine. Drying over $Na_2SO_4$ and purification on silica ($CHCl_3/CH_3OH$, 95:5) afforded the title compound (2.98 g, 91%) as a light yellow oil: MS (ES) m/e 309 (M+H)$^+$.

b) 4-amino-3-[(ethoxy-N-methylcarbonylamino)methyl] benzoic acid trifluoro acetate To a stirred solution of t-butyl-4-amino-3-[(2-hydroxy-4, N-dimethylpentanoylamino)methyl]benzoic acid (2.98 g, 9.67 mmole) in $CH_2Cl_2$ (20 mL) at RT was added TFA (20 mL). After 12 hr, the reaction contents were concentrated, washed with hexanes and dried under high vacuum overnight affording the title compound as an orange oil (3.51 g, 9.60 mmol). This product was used without further purification: MS (ES) m/e 253 (M+H-TFA)$^+$.

Preparation 8
Preparation of 4-amino-3-[(2-hydroxy-N-methylacetylamino)methyl]benzoic acid a) tert-Butyl 4-nitro-3-[(2-hydroxy-N-methylacetylamino)methyl]benzoate To a stirred solution of t-butyl-3-[N-(methyl)aminomethyl]-4-amino benzoate (7.0 g, 26.3 mmole) in DMF (30 mL) at RT was added diisopropylethyl amine (5.0 mL, 28.9 mmole), HOBt (3.90 g, 28.9 mmole), 2-hydroxyacetic acid (2.2 g, 28.9 mmole) and finally EDC (5.54 g, 28.9 mmole). After 12 hr, the reaction contents were poured onto $H_2O$ (200 mL) and extracted with EtOAc (2×150 mL). The organic phases were combined and sequentially washed with $H_2O$ (100 mL) and brine. Drying over $Na_2SO_4$ and purification on silica ($CHCl_3/CH_3OH$, 95:5) afforded the title compound (7.92 g, 93%) as a light yellow oil: MS (ES) m/e 325 (M+H)$^+$.

b) tert-Butyl 4-amino-3-[(2-hydroxy-N-methylacetylamino)methyl]benzoate

To a solution of t-butyl-4-nitro-3-[(2-hydroxy-N-methylacetylamino)methyl]benzoate (7.92 g, 23.15 mmole) in $CH_3OH$ (25 mL) and EtOAc (25 mL) in a Parr hydrogenation flask was added 10% Pd/C (0.20 g). The contents were shaken on a Parr shaker under $H_2$ (50 psi) for 4 hours. The suspension was filtered through celite, concentrated under vacuum and washed with $Et_2O$ to afford the title compound as a light orange foam which was used without further purification: MS (ES) m/e 295 (M+H)$^+$.

Preparation 9
Preparation of 4-amino-3-[(2-hydroxy-3-indol-3-yl-N-methylpropanoylamino)methyl]benzoic acid trifluoro acetate a) tert-Butyl 4-amino-3-[(2-hydroxy-3-indol-3-yl-N-methylpropanoylamino)methyl]benzoic acid To a stirred solution of t-butyl-3-[N-(methyl)aminomethyl]-4-amino benzoate (0.60 g, 2.52 mmole), from Procedure 5, in DMF (20 mL) at RT was added diisopropylethyl amine (0.88 mL, 5.03 mmole), HOBt (0.37 g, 2.77 mmole), DL-3-indolelactic acid (0.57 g, 2.77 mmole) and finally EDC (0.53 g, 2.77 mmole). After 12 hr, the reaction contents were poured onto $H_2O$ (100 mL) and extracted with EtOAc (2×100 mL). The organic phases were combined and sequentially washed with $H_2O$ (100 mL) and brine. Drying over $Na_2SO_4$ and purification on silica ($CHCl_3/CH_3OH$, 95:5) afforded the title compound (0.99 g, 93%) as a light yellow oil: MS (ES) m/e 425 (M+H)$^+$.

b) 4-Amino-3-[(2-hydroxy-3-indol-3-yl-N-methylpropanoylamino)methyl]benzoic acid trifluoro acetate To a stirred solution of t-butyl-4-amino-3-[(2-hydroxy-3-indol-3-yl-N-methylpropanoylamino)methyl]benzoic acid (0.99 g, 2.34 mmole) in $CH_2Cl_2$ (20 mL) at RT was added TFA (20 mL). After 12 hr, the reaction contents were evaporated, washed with $Et_2O$ and dried under high vacuum overnight affording the title compound (0.86 g, 2.34 mmol) as a pink solid. This product was used without further purification: MS (ES) m/e 369 (M+H-TFA)$^+$.

Preparation 10
Preparation of 4-amino-3-[(2-cyclopentyl-N-methylacetylamino)methyl]benzoic acid trifluoro acetate a) tert-Butyl 4-amino-3-[(2-cyclopentyl-N-methylacetylamino)methyl]benzoic acid To a stirred solution of t-butyl-3-[N-(methyl)aminomethyl]-4-amino benzoate (0.55 g, 2.32 mmole), from Procedure 5, in DMF (20 mL) at RT was added diisopropylethyl amine (0.81 mL, 4.64 mmole), HOBt (0.34 g, 2.55 mmole), cyclopentane acetic acid (0.33 g, 2.55 mmole) and finally EDC (0.49 g, 2.55 mmole). After 12 hr, the reaction contents were poured onto $H_2O$ (100 mL) and extracted with EtOAc (2×100 mL). The organic phases were combined and sequentially washed with $H_2O$ (100 mL) and brine. Drying over $Na_2SO_4$ and purification on silica ($CHCl_3/CH_3OH$, 95:5) afforded the title compound (0.75 g, 94%) as a light yellow oil: MS (ES) m/e 348 (M+H)$^+$.

b) 4-Amino-3-[(2-cyclopentyl-N-methylacetylamino)methyl]benzoic acid trifluoro acetate To a stirred solution of t-butyl-4-amino-3-[(2-cyclopentyl-N-methylacetylamino)methyl]benzoic acid (0.75 g, 2.16 mmole) in $CH_2Cl_2$ (20 mL) at RT was added TFA (20 mL). After 12 hr, the reaction contents were evaporated, washed with hexanes and dried under high vacuum overnight affording the title compound (0.63 g, 2.16 mmol) as an orange oil. This product was used without further purification: MS (ES) m/e 292 (M+H-TFA)$^+$.

Preparation 11
Preparation of {4-amino-3-[(methylamino)methyl]phenyl}-N-methyl-N-[(1-methylindol-2-yl)methyl]carboxamide a) t-Butyl-4-nitro-3-{[(N-methyl(phenylmethoxy)carbonylamino]methyl}benzoate To a stirred solution of t-butyl-3-[N-(methyl)aminomethyl]-4-nitro benzoate (11.97 g, 45.0 mmole), from Procedure 3b, in DMF (100 mL) at RT was added triethyl amine (7.27 mL, 52.2 mmole), and N-(benzyloxycarbonyloxy)succinamide (13.0 g, 52.2 mmole). After 12 hr, the reaction contents were poured onto $H_2O$ (200 mL) and extracted with EtOAc (2×200 mL). The organic phases were combined and sequentially washed with $H_2O$ (100 mL) and brine. Drying over $Na_2SO_4$ and purification on silica (hexanes/EtOAc, 1:1) afforded the title compound (17.46 g, 96%) as a light yellow oil: MS (ES) m/e 401 (M+H)$^+$.

b) 4-nitro-3-{[(N-methyl(phenylmethoxy)carbonylamino]methyl}benzoic acid

To a stirred solution of t-butyl-4-nitro-3-{[(N-methyl(phenylmethoxy)carbonylamino]methyl}benzoate (17.46 g, 43.65 mmole) in $CH_2Cl_2$ (100 mL) at RT was added TFA (50 mL). After 12 hr, the reaction contents were evaporated, washed with hexanes and dried under high vacuum overnight to afford the title compound (14.62 g, 42.5 mmol) as an orange oil. This product was used without further purification: MS (ES) m/e 345 (M+H)$^+$.

c) N-[(2-nitro-5-{(N-methyl-N-[(1-methylindol-2-yl)methyl]carbamoyl}phenyl)methyl]-N-methyl(phenylmethoxy)carboxamide To a stirred solution of 4-nitro-3-{[(N-methyl(phenylmethoxy)carbonylamino]methyl}benzoic acid (4.56 g, 13.26 mmole) in DMF (20 mL) at RT was added diisopropylethyl amine (2.31 mL, 13.26 mmole), HOBt (1.79 g, 13.26 mmole), 1-methyl-2-(methylaminomethyl)indole (2.1 g, 12.0 mmole) and finally EDC (2.54 g, 13.26 mmole). After 12 hr, the reaction contents were poured onto $H_2O$ (100 mL) and extracted with EtOAc (2×100 mL). The organic phases were combined and sequentially washed with $H_2O$ (100 mL) and brine. Drying over $Na_2SO_4$ and purification on silica (hexanes/EtOAc, 1:1) afforded the title compound (5.52 g, 92%) as a viscous yellow oil: MS (ES) m/e 501 (M+H)$^+$.

d) {4-amino-3-[(methylamino)methyl]phenyl}-N-methyl-N-[(1-methylindol-2-yl)methyl]carboxamide To a solution of N-[(2-nitro-5-{N-methyl-N-[(1-methylindol-2-yl)methyl]carbamoyl}phenyl)methyl]-N-methyl(phenylmethoxy)carboxamide (6.1 g, 12.2 mmole) in $CH_3OH$ (50 mL) contained in a Parr hydrogenation flask was added a 0.75 g of 10% Pd/C. The contents were shaken on a Parr shaker under $H_2$ (50 psi) for 6 hours. The suspension was filtered through celite and concentrated under vacuum. Purification on silica [$CHCl_3/CH_3OH$ (containing 5% $NH_4OH$), 9:1] afforded the title compound 5 (3.40 g, 83%) as a viscous yellow oil: MS (ES) m/e 337 $(M+H)^+$.

The following examples illustrate methods for preparing the biologically active compounds of this invention from intermediate compounds such as those described in the foregoing Preparations.

Example 1
Preparation of N-[(2-amino-5-{N-methyl-N-[(1-methylindol-2-yl)methyl]carbamoyl}phenyl)methyl]-N-phenylacetamide a) tert-Butyl 3-[(phenylamino)methyl]-4-nitro benzoate To a solution of the crude t-butyl-3-bromomethyl-4-nitro benzoate (2.0 g, 6.3 mmole), from Procedure 3b, in THF (25 mL) at RT was added aniline (2.0 mL, 21.9 mmole). The reaction contents were concentrated, dissolved in EtOAc and washed sequentially with 10% aqueous $NaHCO_3$ and brine. Purification on silica afforded the title compound (1.95 g, 94%) as an orange solid: MS (ES) m/e 429 $(M+H)^+$.

b) {3-[(phenylamino)methyl]phenyl-4-nitro}-N-methyl-N-[(1-methylindol-2-yl)methyl]carboxamide To a stirred solution of tert-butyl 3-[(phenylamino) methyl]-4-nitro benzoate (1.95 g, 4.55 mmole) in $CHCl_2$ (20 mL) at RT was added TFA (20 mL). After 12 hr, the reaction contents were concentrated, treated with 4M aqueous HCl, dioxane (10 mL) and concentrated under vacuum affording a tan solid. The solid residue was washed with hexanes and dried under high vacuum. This product was used directly in the next step without further purification.

To a stirred solution of the above compound in DMF (30 mL) at RT was added diethyl amine (1.7 mL, 12.1 mmole), 1-methyl-2-(methylaminomethyl)indole (1.0 g, 6.0 mmole), HOBt (0.81 g, 6.0 mmole) and finally EDC (1.15 g, 6.0 mmole). After 12 hr, the reaction contents were poured onto $H_2O$ (100 mL) and extracted with EtOAc (2×100 mL). The organic phases were combined and sequentially washed with $H_2O$ (100 mL) and brine. Drying over $Na_2SO_4$ and purification on silica (EtOAc) afforded the title compound (2.33 g, 92%) as a solid yellow foam: MS (ES) m/e 429 $(M+H)^+$.

c) N-[(2-nitro-5-{N-methyl-N-[(1-methylindol-2-yl) methyl]carbamoyl}phenyl)methyl]-N-phenylacetamide To a solution of {3-[(phenylamino)methyl]phenyl-4-nitro}-N-methyl-N-[(1-methylindol-2-yl)methyl] carboxamide (0.75 g, 1.8 mmole) in $CHCl_3$ (10 mL) at 45° C. was added acetic anhydride (0.38 mL, 4.2 mmole) followed by pyridine (0.30 ml, 3.8 mmole). After 12 hr, the reaction solution was concentrated under vacuum, dissolved in EtOAc and sequentially washed with 1 M HCl, and brine. Drying over $Na_2SO_4$ and purification on silica (EtOAc) afforded the title compound (0.82 g, 92%) as a yellow foam: MS (ES) m/e 493 $(M+Na)^+$.

d) N-[(2-amino-5-{N-methyl-N-[(1-methylindol-2-yl) methyl]carbamoyl}phenyl)methyl]-N-phenylacetamide To a solution of N-[(2-nitro-5-{N-methyl-N-[(1-methylindol-2-yl)methyl]carbamoyl}phenyl)methyl]-N-phenylacetamide (0.82 g, 1.7 mmole) in $CH_3OH$ (50 mL) in a Parr hydrogenation flask was added 10% Pd/C (0.50 g). The contents were shaken on a Parr shaker under $H_2$ (50 psi) for 4 hours. The reaction suspension was filtered through celite and concentrated under vacuum. Purification on silica ($CHCl_3/CH_3OH$, 95:5) afforded the title compound (0.51 g, 68%) as an off-white solid: MS (ES) m/e 441 $(M+H)^+$.

Example 2
Preparation of N-[(2-amino-5-{N-methyl-N-[(1-methylindol-2-yl)methyl]carbamoyl}phenyl)methyl]-N-methylacetamide To a stirred solution of 4-amino-3-[(N-methylacetylamino)methyl]benzoic acid trifluoro acetate (0.73 g, 2.17 mmole), from Procedure 3, in DMF (20 mL) at RT was added diisopropylethyl amine (0.83 ml, 4.78 mmole), HOBt (0.32 g, 2.39 mmole), 1-methyl-2-(methylaminomethyl)indole (0.40 g, 2.39 mmole) and finally EDC (0.45 g, 2.39 mmole). After 12 hr, the reaction contents were poured onto $H_2O$ (100 mL) and extracted with EtOAc (2×100 mL). The organic phases were combined and sequentially washed with $H_2O$ (100 mL) and brine. Drying over $Na_2SO_4$ and purification on silica ($CHCl_3/CH_3OH$. 95:5) afforded the title compound (0.73 g, 89%) as a light yellow solid: MS (ES) m/e 379 $(M+H)^+$.

Example 3
Preparation of N-[(2-amino-5-{N-methyl-N-[(1-methylindol-2-yl)methyl]carbamoyl}phenyl)methyl]-N-(2-phenylethyl)acetamide According to the procedure of Example 2, except substituting 4-amino-3-[(N-phenethylacetylamino)methyl] benzoic acid (0.60 g, 1.92 mmole) for 4-amino-3-[(N-methylacetylamino)methyl]benzoic acid trifluoro acetate, the title compound (0.83 g, 92%) was prepared as a yellow solid following chromatography on silica gel ($CHCl_3/CH_3OH$. 95:5): MS (ES) m/e 469 $(M+H)^+$.

Example 4
Preparation of N-[(2-amino-5-{N-methyl-N-[(1-methylindol-2-yl)methyl]carbamoyl}phenyl)methyl]-2-hydroxy-4-methyl-N-methylpentanamide According to the procedure of Example 2, except substituting 4-amino-3-[(2-hydroxy-4,N-dimethylpentanoylamino)methyl]benzoic acid trifluoro acetate (2.1 g, 5.1 mmole) for 4-amino-3-[(N-methylacetylamino)methyl]benzoic acid trifluoro acetate, the title compound (2.06 g, 90%) was prepared as a yellow foam following chromatography on silica gel ($CHCl_3/CH_3OH$, 95:5): MS (ES) m/e 451 $(M+H)^+$.

Example 5
Preparation of {4-amino-3-[(ethoxy-N-methylcarbonylamino)methyl]phenyl}-N-methyl-N-[(1-methylindol-2-yl)methyl]carboxamide According to the procedure of Example 2, except substituting 4-amino-3-[(ethoxy-N-methylcarbonylamino) methyl]benzoic acid trifluoro acetate (0.75 g, 2.05 mmole) for 4-amino-3-[(N-methylacetylamino)methyl]benzoic acid trifluoro acetate, the title compound (0.75 g, 90%) was prepared as a tan foam following chromatography on silica gel ($CHCl_3/CH_3OH$, 95:5): MS (ES) m/e 409 $(M+H)^+$.

Example 6
Preparation of N-[(2-amino-5-{N-methyl-N-[(1-methylindol-2-yl)methyl]carbamoyl}phenyl)methyl]-2-hydroxy-N-methylacetamide According to the procedure of Example 2, except substituting 4-amino-3-[(2-hydroxy-N-methylacetylamino) methyl]benzoic acid (1.0 g, 2.84 mmole) for 4-amino-3-[(N-methylacetylamino)methyl]benzoic acid trifluoro acetate, the title compound (0.99 g, 88%) was prepared as an off-white solid following chromatography on silica gel ($CHCl_3/CH_3OH$, 95:5): MS (ES) m/e 395 $(M+H)^+$.

Example 7
Preparation of N-[(2-amino-5-{N-methyl-N-[(1-methylindol-3-yl)methyl]carbamoyl}phenyl)methyl]-N-methylacetamide According to the procedure of Example 2, except substituting 4-amino-3-[(N-methylacetylamino)methyl]benzoic acid trifluoroacetate (0.44 g, 1.31 mmole) for 4-amino-3-[(N-methylacetylamino)methyl]benzoic acid trifluoro acetate, the title compound (0.45 g, 92%) was prepared as an off-white solid following chromatography on silica gel (CHCl$_3$/CH$_3$OH, 95:5): MS (ES) m/e 379 (M+H)$^+$.

Example 8
Preparation of N-[(2-amino-5-{N-methyl-N-[(1-methylindol-2-yl)methyl]carbamoyl}phenyl)methyl]-2-hydroxy-3-indol-3-yl-N-methylpropanamide According to the procedure of Example 2, except substituting 4-amino-3-[(2-hydroxy-3-indol-3-yl-N-methylpropanoylamino)methyl]benzoic acid trifluoro acetate (0.41 g, 1.12 mmole) for 4-amino-3-[(N-methylacetylamino)methyl]benzoic acid trifluoro acetate, the title compound (0.46 g, 78%) was prepared as an off-white solid following chromatography on silica gel (CHCl$_3$/CH$_3$OH, 95:5): MS (ES) m/e 524 (M+H)$^+$.

Example 9
Preparation of N-[(2-amino-5-{N-methyl-N-[(1-methylindol-2-yl)methyl]carbamoyl}phenyl)methyl]-2-cyclopentyl-N-methylacetamide According to the procedure of Example 2, except substituting 4-amino-3-[(2-cyclopentyl-N-methylacetylamino)methyl]benzoic acid trifluoro acetate (1.05 g, 3.60 mmole) for 4-amino-3-[(N-methylacetylamino)methyl]benzoic acid trifluoro acetate, the title compound (1.45 g, 90%) was prepared as an off-white solid following chromatography on silica gel (hexanes/EtOAc, 1:2): MS (ES) m/e 448 (M+H)$^+$.

Example 10
Preparation of {4-amino-3-{[(4-hydroxyphenyl)-N-methylcarbonylamino]methyl}phenyl}-N-methyl-N-[(1-methylindol-2-yl)methyl]carboxamide According to the procedure of Example 2, except substituting 4-hydroxybenzoic acid (0.23 g, 1.64 mmole) for 4-amino-3-[(N-methylacetylamino)methyl]benzoic acid trifluoro acetate and substituting {4-amino-3-[(methylaminomethyl)phenyl}-N-methyl-N-[(1-methylindol-2-yl)methyl]carboxamide (0.50 g, 1.49 mmole) for 1-methyl-2-(methylaminomethyl)indole, the title compound (0.62 g, 92%) was prepared as an off-white solid following chromatography on silica gel (CHCl$_3$/CH$_3$OH, 95:5): MS (ES) m/e 457 (M+H)$^+$.

Example 11
Preparation of N-[(2-amino-5-{N-methyl-N-[(1-methylindol-2-yl)methyl]carbamoyl}phenyl)methyl]-N-methyl-3-(phenylsulfonyl)propanamide According to the procedure of Example 2, except substituting 3-(phenylsulfonyl)propionic acid (0.35 g, 1.64 mmole) for 4-amino-3-[(N-methylacetylamino)methyl] benzoic acid trifluoro acetate and substituting {4-amino-3-[(methylaminomethyl)phenyl}-N-methyl-N-[(1-methylindol-2-yl)methyl]carboxamide (0.50 g, 1.49 mmole) for 1-methyl-2-(methylaminomethyl)indole, the title compound (0.72 g, 91%) was prepared as an off-white solid following chromatography on silica gel (CHCl$_3$/CH$_3$OH, 95:5): MS (ES) m/e 533 (M+H)$^+$.

Example 12
Parenteral Dosage Unit Composition

A preparation which contains 20 mg of the compound of Example 1 as a sterile dry powder is prepared as follows: 20 mg of the compound is dissolved in 15 mL of distilled water. The solution is filtered under sterile conditions into a 25 mL multi-dose ampoule and lyophilized. The powder is reconstituted by addition of 20 mL of 5% dextrose in water (D5W) for intravenous or intramuscular injection. The dosage is thereby determined by the injection volume. Subsequent dilution may be made by addition of a metered volume of this dosage unit to another volume of D5W for injection, or a metered dose may be added to another mechanism for dispensing the drug, as in a bottle or bag for IV drip infusion or other injection-infusion system.

Example 13
Oral Dosage Unit Composition

A capsule for oral administration is prepared by mixing and milling 50 mg of the compound of Example 1 with 75 mg of lactose and 5 mg of magnesium stearate. The resulting powder is screened and filled into a hard gelatin capsule.

Example 14
Oral Dosage Unit Composition

A tablet for oral administration is prepared by mixing and granulating 20 mg of sucrose, 150 mg of calcium sulfate dihydrate and 50 mg of the compound of Example 1 with a 10% gelatin solution. The wet granules are screened, dried, mixed with 10 mg starch, 5 mg talc and 3 mg stearic acid; and compressed into a tablet.

The above description fully discloses how to make and use the present invention. However, the present invention is not limited to the particular embodiments described hereinabove, but includes all modifications thereof within the scope of the following claims. The various references to journals, patents and other publications which are cited herein comprises the state of the art and are incorporated herein by reference as though fully set forth.

---

What is claimed is:

1. A compound according to formula (I):

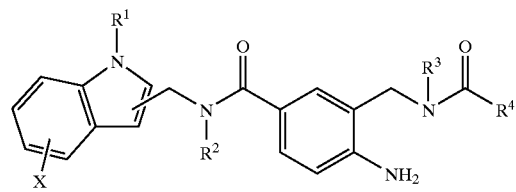

wherein:

$R^1$ is $C_{1-4}$alkyl;

$R^2$ is $C_{1-4}$alkyl;

$R^3$ is —$C_{1-4}$alkyl, —$C_{0-4}$alkyl-Ar or —$C_{0-4}$alkyl-Het, $R^4$ is —$C_{1-4}$alkyl, —$(CH_2)_{1-4}$OH, —$OC_{1-4}$alkyl, —$SC_{1-4}$alkyl, —$N(C_{1-4}$alkyl$)_2$, —$C_{0-4}$alkyl-Ar, —$C_{0-4}$alkyl-Het, —$C_{0-4}$alkyl-$C_{3-6}$cycloalkyl, —CH(OH)—$CH_{2-R^*}$ or —$(CH_2)_{1-3}SO_2$Ar;

$R^*$ is $C_{1-4}$alkyl, Ar or Het;

X is H, $C_{1-4}$alkyl, OR', SR', CN, N(R')$_2$, CH$_2$N(R')$_2$, NO$_2$, CF$_3$, CO$_2$R', CON(R')$_2$, COR', NR'C(O)R', F, Cl, Br, I, or —S(O)$_r$CF$_3$;

R' is H, $C_{1-6}$alkyl or —$C_{0-6}$alkyl-Ar; and r is 0, 1 or 2;

or a pharmaceutically acceptable salt thereof.

2. A compound according to claim 1 of formula (Ia):

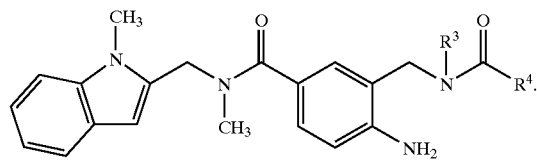

3. A compound according to claim 1 in which $R^3$ is $C_{1-4}$alkyl or —$C_{0-2}$alkyl-Ph.

4. A compound according to claim 1 in which $R^4$ is —$C_{1-4}$alkyl, —CH$_2$OH, —$OC_{1-4}$alkyl, —$C_{0-2}$alkyl-Ph, —$C_{0-2}$alkyl-$C_{3-6}$cycloalkyl, —CH(OH)—CH$_2$—$R^*$ or —(CH$_2$)$_2$SO$_2$Ph.

5. A compound according to claim 1 which is:

N-[(2-amino-5-{N-methyl-N-[(1-methylindol-2-yl)methyl]carbamoyl}phenyl)methyl]-N-methylacetamide;

N-[(2-amino-5-{N-methyl-N-[(1-methylindol-2-yl)methyl]carbamoyl}phenyl)methyl]-N-(2-phenylethyl)acetamide;

N-[(2-amino-5-{N-methyl-N-[(1-methylindol-2-yl)methyl]carbamoyl}phenyl)methyl]-2-hydroxy-4-methyl-N-methylpentanamide;

{4-amino-3-[(ethoxy-N-methylcarbonylamino)methyl]phenyl}-N-methyl-N-[(1-methylindol-2-yl)methyl]carboxamide;

N-[(2-amino-5-{N-methyl-N-[(1-methylindol-2-yl)methyl]carbamoyl}phenyl)methyl]-2-hydroxy-N-methylacetamide;

N-[(2-amino-5-{N-methyl-N-[(1-methylindol-3-yl)methyl]carbamoyl}phenyl)methyl]-N-methylacetamide;

N-[(2-amino-5-{N-methyl-N-[(1-methylindol-2-yl)methyl]carbamoyl}phenyl)methyl]-N-phenylacetamide;

N-[(2-amino-5-{N-methyl-N-[(1-methylindol-2-yl)methyl]carbamoyl}phenyl)methyl]-2-hydroxy-3-indol-3-yl-N-methylpropanamide;

(4-amino-3-{[(4-hydroxyphenyl)-N-methylcarbonylamino]methyl}phenyl)-N-methyl-N-[(1-methylindol-2-yl)methyl]carboxamide;

N-[(2-amino-5-{N-methyl-N-[(1-methylindol-2-yl)methyl]carbamoyl}phenyl)methyl]-N-methyl-3-(phenylsulfonyl)propanamide; or N-[(2-amino-5-{N-methyl-N-[(1-methylindol-2-yl)methyl]carbamoyl}phenyl)methyl]-2-cyclopentyl-N-methylacetamide;

or a pharmaceutically acceptable salt thereof.

6. A pharmaceutical composition which comprises a compound according to claim 1 and a pharmaceutically acceptable carrier.

7. A method for inhibiting FabI which comprises administering to a subject in need thereof a compound according to claim 1.

8. A method of treating bacterial infections which comprises administering to a subject in need thereof a compound according to claim 1.

9. A process for preparing compounds of formula (I) as defined in claim 1, which process comprises reacting a compound of formula (II) with a compound of formula (III):

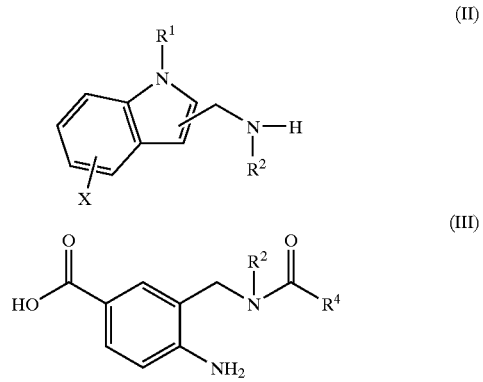

wherein $R^1$, $R^2$, $R^3$, $R^4$ and X are as defined in formula (I), with any reactive functional groups protected, in the presence of EDC and HOBT;

and thereafter removing any protecting groups, and optionally forming a pharmaceutically acceptable salt.

* * * * *